United States Patent [19]

Graham et al.

[11] 4,053,602

[45] Oct. 11, 1977

[54] COMPOSITIONS FOR TREATING COCCIDIOSIS CONTAINING 5-DEAZARIBOFLAVIN AND ITS DERIVATIVES

[75] Inventors: Donald W. Graham, Mountainside; Edward F. Rogers, Middletown; Wallace T. Ashton, Clark, all of N.J.

[73] Assignee: Merck & Co., Inc., Rahway, N.J.

[21] Appl. No.: 737,890

[22] Filed: Nov. 2, 1976

[51] Int. Cl.$^2$ .................. A61K 31/505; A61K 31/675
[52] U.S. Cl. ...................................... 424/251; 424/200
[58] Field of Search .............................. 424/251, 200; 260/256.4 F

[56] References Cited
U.S. PATENT DOCUMENTS 3,868,374   2/1975   Yale et al. ..................... 260/256.4 F

OTHER PUBLICATIONS

O'Brien et al., Chem. Abst. vol. 68, (1968), p. 96076g.

*Primary Examiner*—Sam Rosen
*Attorney, Agent, or Firm*—Walter Patton; J. Jerome Behan

[57] ABSTRACT

5-Deazariboflavin, its phosphate ester and non-toxic salts thereof and its novel bis(loweralkoxymethylene) derivatives have antiprotozoal and antiparasitic activity. They are particularly useful for controlling cecal and/or intestinal coccidiosis when administered in minor quantities to animals, in particular to poultry, usually in admixture with animal sustenance. The compounds are included in compositions useful for the prevention and treatment of coccidiosis in poultry.

11 Claims, No Drawings

COMPOSITIONS FOR TREATING COCCIDIOSIS CONTAINING 5-DEAZARIBOFLAVIN AND ITS DERIVATIVES

BACKGROUND OF THE INVENTION

Coccidiosis is a widespread poultry disease which is produced by infections of protozoa of the genus Eimeria which causes severe pathology in the intestines and ceca of poultry. Some of the most significant of these species are E. tenella, E. acervulina, E. necatrix, E. brunetti and E. maxima. This disease is generally spread by the birds picking up the infectious organism in droppings on contaminated litter or ground, or by way of food or drinking water. The disease is manifested by hemorrhage, accumulation of blood in the ceca, passage of blood in the droppings, weakness and digestive disturbances. The disease often terminates in the death of the animal, but the fowl which survive severe infections have had their market value substantially reduced as a result of the infection. Coccidiosis is, therefore, a disease of great economic importance and extensive work has been done to find new and improved methods for controlling and treating coccidial infections in poultry.

Trypanosomiasis is a term used to describe a group of allied protozoal diseases, each of which is due to infection with a species of the genus Trypanosoma. They reach their greatest importance in Africa where their presence in enzootic form precludes the keeping of domestic animals throughout the largest part of the continent between 15° N and 20° S latitude. The pathogenic trypanosomes of Africa are considered to be primarily associated with the tsetse flies (glossina) which feed on vertebrate blood. Wherever tsetse are present, trypanosomiasis will also be found in some part of the mammalian population. The clinical findings are typically those of a wasting disease with intermittent fever. Anemia, edema, and cachexia are parts of the syndrome.

The important trypanosomes pathogenic to domestic animals are T. congolense, T. simiae, T. vivax, and T. brucei. The latter trypanosome is morphologically identical to T. gambiense, responsible for human "sleeping sickness" of Africa. A trypanosome found in the Western Hemisphere is T. cruzi, which affects both domestic animals and man.

Malaria is a serious parasitic infection normally transmitted by the bite of an infected anopheles mosquito, although it may also be produced by transfusion of blood from an infected donor. It is found most frequently in the tropics and in some tropical areas is hyperendemic. In man it is caused most frequently by the parasites Plasmodium falciparum, P. vivax and P. malariae. The acute phase of the disease is characterized by shaking chills, high fever, sweats and headache. With malaria due to P. vivax and P. malariae the patient frequently suffers relapse because of the ability of these parasites to harbor in liver cells for extended periods of time. In view of the recurrent nature of the disease, chemotherapy is used not only to treat the acute phases, but also on an extended basis as a prophylactic or suppressive therapy. Although there are now available synthetic chemicals for the treatment of malaria, the search has continued for new and/or improved antimalarials and for compounds effective against strains of Plasmodia resistant to currently available agents.

SUMMARY OF THE INVENTION

This invention is based on the discovery that 5-deazariboflavin, its 5'-phosphate ester and non-toxic salts thereof and the novel 2', 3',4',5'-di-O-loweralkoxymethylene derivatives of 5-deazariboflavin have a surprisingly and unexpectedly high degree of activity against coccidiosis of poultry. Administering a small amount of these compounds, preferably in combination with poultry feed, is effective in preventing or greatly reducing the incidence of coccidiosis. The compounds are effective against both the cecal form (caused by E. tenella) and the intestinal forms (principally caused by E. acervulina, E. brunetti, E. maxima and E. necatrix) of coccidiosis.

This invention relates generally to the usefulness of 5-deazariboflavin, its 5'-phosphate ester and non-toxic salts thereof and the novel 2',3',4',5'-di-O-loweralkoxymethylene derivatives of 5-deazariboflavin for the treatment and prevention of coccidiosis in susceptible animals especially in fowl, and particularly in poultry. This invention relates also to the usefulness of these compounds against other protozoal infections especially against human and animal trypanosomiasis and malaria. This invention still further relates to the novel 2', 3',4',5'-di-O-loweralkoxymethylene derivatives of 5-deazariboflavin and the method of preparation and use of the same in the control and treatment of coccidiosis.

In addition, this invention relates to compositions including these compounds as the active ingredient, intimately admixed with an inert carrier for administration to animals infected with coccidia. It is therefore, an object of this invention to provide a method of treatment for coccidiosis using the above compounds. It is also an object of this invention to include these compounds or mixtures thereof in compositions for administration to poultry which compositions are employed to treat coccidiosis. Another object is to provide the novel 2',3',4',5'-di-O-loweralkoxymethylene derivatives of 5-deazariboflavin which are useful in the treatment of coccidiosis. As used herein, the term "treat" includes administration to animals which have developed active symptoms of coccidiosis, as well as animals without overt symptoms, but that have been exposed to causative organisms. Further objects will become apparent upon a further reading of the description.

5-Deazariboflavin and the method for preparing it are described in D. O'Brien et al., J. Heterocycl. Chem. 7, 99 (1970). 5-Deazariboflavin-5'-phosphate and the method for preparing it are described in D. Edmondson et al., Biochemistry, 11, 1133 (1972).

5-Deazariboflavin has the structure:

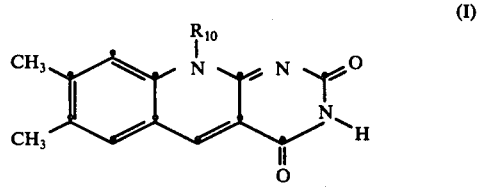

(I)

wherein $R_{10}$ is:

—CH$_2$—(CHOH)$_3$—CH$_2$OR$_5$ wherein R$_5$ is H.

5-Deazariboflavin-5'-phosphate corresponds to the case wherein $R_5$ is

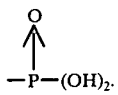

The novel compounds of the present invention, 2',3',4',5'-di-O-loweralkoxymethylene derivatives of 5-deazariboflavin have the structure.

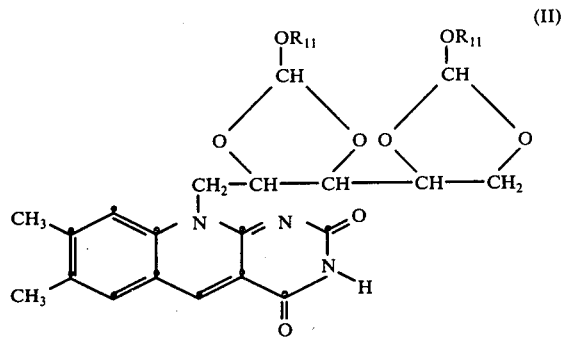

wherein $R_{11}$ is an alkyl group containing 1 to 5 carbon atoms. The preferred embodiments of compound (II) of the present invention are those wherein $R_{11}$ is methyl or ethyl, designated 2',3',4',5'-di-O-methoxymethylene-5-deazariboflavin and 2',3',4',5'-di-O-ethoxymethylene-5-deazariboflavin, respectively.

Included in the scope of the present invention is the use of the non-toxic salts of 5-deazariboflavin-5'-phosphate as anticoccidial agents. The non-toxic salts may be inorganic or organic. Representative examples of salts of inorganic bases that might be mentioned are alkali metal or alkaline earth metal salts such as sodium, potassium and calcium. Representative examples of salts of organic bases that might be mentioned are primary, secondary and tertiary amines, for example, monoalkylamines, dialkylamines, trialkylamines, alkyldiamines, and nitrogen-containing heterocyclic amines.

5-Deazariboflavin-5'-phosphate is a water soluble acidic substance which reacts with salt forming substances, such as inorganic and organic bases, to form salts of the phosphate group. Thus, upon reaction with alkali metal and alkaline earth metal hydroxides, carbonates, bicarbonates, the corresponding alkali metal or alkaline earth metal salt is obtained. Other metal salts such as iron and the like can be similarly prepared by metathesis or in accordance with other methods well known to those skilled in this art. Similarly, salts of organic bases, such as primary, secondary and tertiary amines, for example, monoalkylamines, dialkylamines, trialkylamines, alkyldiamines, and nitrogen-containing heterocyclic amines, are prepared in accordance with methods known in this art. The salts can be mono salts such as the monosodium salt obtained, for example, by reacting one equivalent of sodium hydroxide with one equivalent of acid; disalts obtained, for example, by reacting two equivalents of sodium hydroxide with one equivalent of the acid; mixed disalts obtained by reacting one equivalent of the monosalt with one equivalent of a second base; diphosphate salts obtained, for example, by reacting one equivalent of calcium hydroxide with two equivalents of the acid; mixed salts such as calcium hydrogen lactate obtained by reacting one equivalent of lactic acid with the calcium diphosphate salt and the like.

The novel bis(loweralkoxymethylene) derivatives of 5-deazariboflavin are prepared by refluxing a suspension of 5-deazariboflavin with excess triloweralkylorthoformate. The triloweralkylorthoformate can serve both as a reactant and a solvent. Sufficient suitable cosolvent may be added at reflux to dissolve the starting material. The reaction is preferably carried out in the presence of a strong acid catalyst. Suitable strong acid catalysts include aromatic or aliphatic sulfonic acids, such as, benzenesulfonic acid, naphthalenesulfonic acid, methanesulfonic acid and ethanesulfonic acid. Sulfuric acid or anhydrous hydrogen chloride may also be used.

A preferred process for obtaining the novel bis(loweralkoxymethylene) derivatives of 5-deazariboflavin is to reflux 5-deazariboflavin and p-toluenesulfonic acid monohydrate (present to the extent of 5% to 10% by weight with respect to 5-deazariboflavin) in excess triloweralkylorthoformate, such as trimethylorthoformate or triethylorthoformate. Sufficient dimethylsulfoxide (DMSO) is added at reflux to dissolve the starting materials. After a reaction time of about 5 minutes to about 1 hour, the solution is cooled and diluted with the alcohol corresponding to the triloweralkylorthoformate employed in the reaction, i.e., diluted with methanol when trimethylorthoformate is employed or diluted with ethanol when triethylorthoformate is employed. After further cooling and stirring, the product precipitates and is collected by filtration.

It is, therefore, a primary object of this invention to provide novel feed compositions useful for the prevention and suppression of coccidiosis in poultry.

Another object of this invention is to provide a novel anticoccidial agent. Still another object of this invention is to provide the novel bis(loweralkoxymethylene) derivatives of 5-deazariboflavin which are useful in the control of protozoal and parasitic infections.

A further object of this invention is to provide a new and useful method for the control of coccidiosis in poultry which comprises administering to the poultry minor amounts of the anticoccidial substances of this invention.

A still further object of this invention is to provide a method for preparing the novel 2',3',4',5'-di-O-loweralkoxymethylene-5-deazariboflavins.

These and further objects of this invention will become apparent or be described as the description thereof herein proceeds.

DESCRIPTION OF THE PREFERRED EMBODIMENTS

In accordance with this invention, coccidiosis in poultry is controlled or suppressed by administering to the poultry a non-toxic, anticoccidially effective quantity of 5-deazariboflavin or its derivatives hereinabove described.

5-deazariboflavin and its derivatives hereinabove described when used an anticoccidial agents are orally administered to poultry for the control and prevention of coccidiosis. Any number of conventional methods are suitable for administering the coccidiostats of this invention to poultry, as for example, they may be given in the poultry feed or included in drinking water. The actual quantity of the coccidiostats administered to the poultry in accordance with this invention will vary over a wide range and be adjusted to individual needs, depending upon species of the coccidia involved and severity of the infection. The limiting criteria are that the minimum amount is sufficient to control coccidiosis and the maximum amount is such that the coccidiostats do not result in any undesirable effects.

A feed will typically contain from about 0.005 to about 0.25%, preferably from about 0.005 to about 0.05% by weight of 5-deazariboflavin and its derivatives hereinabove described. All the compounds described herein are active at a level of 0.001% by weight. The optimum levels will naturally vary with the species of Eimeria involved, and can be readily determined by one skilled in the art. Levels of 5-deazariboflavin and the derivatives hereinabove described in poultry feed of from about 0.001 to about 0.006% by weight of the diet are especially useful.

The quantity or concentration of 5-deazariboflavin and its derivatives hereinabove described in any admixture in which they are administered to the poultry will, of course, vary in accordance with the type of admixture utilized.

Of the various methods of administering the coccidiostats to poultry, they are most conveniently administered as a component of a feed composition. The coccidiostats may be readily dispersed by mechanically mixing the same in finely ground form with the poultry feedstuff, or with an intermediate formulation (premix) that is subsequently blended with other components to prepare the final poultry feedstuff that is fed to the poultry. Typical components of poultry feedstuffs include molasses, fermentation residues, corn meal, ground and rolled oats, wheat shorts and middlings, alfalfa, clover and meat scraps, together with mineral supplements such as bone meal and calcium carbonate and vitamins.

Suitable compositions also include feed premixes in which the active ingredient is present in relatively large amounts and which are suitable for addition into the feed either directly or after an intermediate dilution or blending step. Such compositions may also be added to the animals feed in the form of a top dressing. Typical carriers or diluents suitable for such compositions include for example, distillers dried grains such as corn distiller's dried grains and corn distiller's grains, corn meal and corn meal germ, citrus metal, fermentation residues, ground oyster sheels, wheat shorts and wheat standard middlings, molasses solubles, corncob meal, edible bean mill feed, soyagrits, crushed limestone and the like. The active compound is intimately dispersed throughout the carrier by methods such as grinding, stirring, milling or tumbling. Compositions containing from about 0.1 to 50% by weight, especially from about 0.5 to 25% by weight of the compound 5-deazariboflavin and its derivatives hereinabove described are particularly suitable as feed premixes.

Examples of typical feed premixes containing 5-deazariboflavin dispersed in a solid inert carrier are:

|   |   | lbs. |
|---|---|------|
| A. | 5-deazariboflavin | 6.0 |
|    | Wheat standard middlings | 94.0 |
| B. | 5-deazariboflavin | 10.0 |
|    | Corn distiller's dried grains | 90.0 |
| C. | 5-deazariboflavin | 20.0 |
|    | Corn germ meal | 30.0 |
|    | Corn distiller's grains | 50.0 |

This invention is not limited to anticoccidial compositions having 5-deazariboflavin and its derivatives hereinabove described as the sole active ingredients. Also contemplated within its scope is what might be called "combined treatment" where 5-deazariboflavin or its derivatives hereinabove described and one or more other anticoccidial agents are administered concurrently. For such purposes, compositions may be prepared containing 5-deazariboflavin or its derivatives hereinabove described admixed with one or more other coccidiostats such as sulfaquinoxaline, other sulfa compounds, 4,4'-dinitrocarbanilide-2-hydroxy-4,6-dimethylpyrimidine complex, 3,3'-dinitrodiphenyldisulfide, 5-nitrofurfural semicarbazone, amprolium, zoalene, buquinolate, ethopabate, monensin, 9-(2-chloro-6-fluorobenzyl)adenine and the like.

The feed may be supplemented by up to 100% of the normal level (3 to 5 ppm) of riboflavin to decrease the toxicity of the 5-deazariboflavin and its derivatives hereinabove described to the chickens without changing the effectiveness of the coccidiostats.

It will likewise be understood by those skilled in this art that special feed supplement formulations and finished animals feeds containing vitamins, antibiotics, growth-promoting agents and other nutritional substances may include 5-deazariboflavin or its derivatives hereinabove described.

5-Deazariboflavin and the derivatives described hereinabove have value in the control of trypanosomiasis in domesticated animals, particularly cattle. For this purpose, they may be administered orally with an ingestible carrier as a component of the animal feedstuff, in the drinking water, in salt blocks and in unit dosage forms such as boluses and drenches. The amount of active ingredient required for optimum control of trypanosomiasis varies in accordance with such factors as the species of animal to be treated, the species of infecting parasite, the severity of infection, and whether the compound is employed therapeutically or prophylactically.

In employing 5-deazariboflavin and the derivatives described hereinabove as antimalarials, the compounds are preferably administered orally. Oral dosage forms such as capsules, tablets or powders in which the drugs are intimately admixed with a non-toxic solid pharmaceutically acceptable carrier or diluent vehicle are preferred. However, liquid formulations such as syrups, suspensions or elixirs may be used if desired. The compounds may also be administered parenterally or intravenously in which case they may be formulated as a solution or suspension in sterile physiologic saline.

As will be understood and appreciated by those skilled in this art, the preferred or optimal dose will depend to some extent upon the species of malaria being treated, the type of treatment being used, i.e., prophylactic or therapeutic. Selection of optimum dose is made without difficulty by a clinician skilled in this art. For example, treatment of acute attacks requires higher and more frequent doses whereas in suppressive or prophylatic therapy lower doses are used but over a longer period of time.

The following non-limiting examples will serve to further illustrate the instant invention.

ANTICOCCIDIAL EFFICACY STUDIES OF 5-DEAZARIBOFLAVIN IN BATTERIES

A. Methods

1. Brooding and Feeding

White Rock male chickens obtained from a commercial hatchery were placed on test at two weeks of age. The chickens were housed in stainless steel, wirefloored batteries in an isolation area. Feed and water were provided without restriction. A commercial nonmedicated laboratory broiler feed was used as the basal ration. The medicated feeds were prepared by adding appropriate amounts of the agents to the basal ration. The agents were uniformly blended in the feed by thorough mixing just prior to use. All groups of experimental chickens were housed in identical batteries in a room with uniform temperature and light control. At two weeks of age, the chickens were weighted and those in the middle of the weight distribution were then divided into 16 groups of 5 chickens, equally balanced according to weights. With the aid of a randomization table, 4 groups were assigned as nonmedicated noninfected controls, 4 groups as infected nonmedicated controls and 8 groups to each of 4 different dietary levels of 5-deazariboflavin.

2. The Infection

The coccidal culture of *E. tenella* used for these studies was a laboratory-maintained strain isolated from field cultures obtained from Australia.

The infectio was produced by suspending the specified number of sporulated oocysts in 1 ml. of water and inoculating them directly into the bird's crop with a special oral dosing needle 48 hours after the medicated diets were fed. The number of oocysts used per bird was as follows:

| Coccidial Infection | No. Oocysts/ml./Bird |
|---|---|
| *E. tenella* | 50,000 |

Throughout the course of the experiment, the chickens were observed daily, any deaths were recorded and intestinal lesions (if present) were scored. The experiment was terminated in 8 days. All surviving birds in each cage were group-weighed, ceca scored and removed.

bers above 175 are indicative of good anticoccidial efficacy and good weight gain.

The Anticoccidial Index is calculated according to the formula:

$$\text{Anticoccidial Index} = \% \text{ Survival} + \text{Relative Weight Gain} - \text{Lesion Index} - \text{Oocyst Index}.$$

The values necessary for determining the Anticoccidial Index is determined as follows:

The Oocyst Index are calculated according to the formula:

$$\text{Oocyst Index} = \frac{\text{Oocysts per Bird} \times 10^6}{\text{Oocysts per Bird} \times 10^6 \text{ of Average Infected Control}} \times 40.$$

Maximum of 40 Oocyst Index may be given to treated pens; no such limit is imposed upon the Infected Controls. To determine the "Oocyst per bird + $10^6$," cecas were homogenized in 100 ml. of water per pen, 5 ml. of each homogenized sample were added to 5 ml. of 1 Normal NaOH solution in test tubes. The contents of each tube were mixed on a cyclo-mixer. The total number of oocysts in 20 fields of vision of a hemocytometer were counted and multiplied by the dilution factor 0.1 and divided by the number of surviving birds.

$$\text{Lesion Index} = \text{Gross Lesions} \times 10.$$

$$\text{Relative Weight Gain} = \frac{\text{Grams Gain}}{\text{Grams Gain of the Average Normal}} \times 100.$$

EXAMPLE 1

Preparation of 2',3',4',5'-Di-O-methoxymethylene-5-deazariboflavin

A suspension of 196 mg. (0.50 mmole) of 5-deazariboflavin and 15 mg. of p-toluenesulfonic acid monohy-

TABLE I

Activity of 5-Deazariboflavin Against *E. tenella*

| | Dose % Diet | % Survival | Relative Weight Gain | Lesion Index | Oocyst Index | Anticoccidial Index |
|---|---|---|---|---|---|---|
| Normal Control | | 100 | 96 | 0 | 2 | 194 |
| Normal Control | | 100 | 104 | 0 | 0 | 204 |
| Infected Control | | 40 | 28 | 36 | 15 | 17 |
| Infected Control | | 60 | 47 | 34 | 65 | 8 |
| | 0.009 | 100 | 86 | 0 | 0 | 186 |
| | 0.006 | 100 | 85 | 0 | 0 | 185 |
| | 0.003 | 100 | 99 | 0 | 0 | 199 |
| | 0.001 | 100 | 97 | 0 | 0 | 197 |
| Normal Control | | 100 | 98 | 0 | 0 | 198 |
| Normal Control | | 100 | 102 | 0 | 0 | 202 |
| Infected Control | | 80 | 53 | 34 | 52 | 47 |
| Infected Control | | 100 | 48 | 28 | 27 | 93 |
| | 0.009 | 100 | 90 | 2 | 0 | 188 |
| | 0.006 | 100 | 86 | 0 | 0 | 186 |
| | 0.003 | 100 | 85 | 0 | 0 | 185 |
| | 0.001 | 100 | 85 | 0 | 1 | 184 |

4. Evaluation

Several objective standards were used for evaluating the anticoccidal activity of the compound tested. These included observations and records on the mortality rate, the growth of the chicks, the severity of pathological lesions produced by the coccidia and the average number of oocysts per bird. These parameters were combined into a single number designated as the Anticoccidial Index set forth in the last column of Table I. The Anticoccidal Index ideally ranges from zero to 200. However, medicated birds that have a relative percent weight gain of greater than 100% can result in an upper index of slightly above 200. Anticoccidial Index numdrate in 5 ml. of trimethylorthoformate was stirred under reflux. DMSO (2.2 ml. total) was added gradually at the boiling point until all the solid had dissolved. After 5 minutes, tlc in (9:1 CHCl$_3$-MeOH) had indicated complete conversion to product. The solution was cooled and diluted to 100 ml. with methanol. Crystallization began rapidly after dilution with methanol. After further cooling and stirring, the product was isolated by filtration and washed with methanol and with ether. Yield of yellow solid = 103 mg., m.p. 277°–279° C. (dec. preliminary softening). Tlc in (9:1 CHCl$_3$-MeOH) showed a single spot. A second crop (20 mg.) had m.p.

275°-277° C. (dec. preliminary softening). Tlc in (9:1 CHCl₃:MeOH) showed a single spot. Total yield = 123 mg. (54%).

EXAMPLE 2

Preparation of 2',3',4',5'-Di-O-ethoxymethylene-5-deazariboflavin

A suspension of 196 mg. (0.50 mmole) of 5-deazariboflavin and 15 mg. of p-toluenesulfonic acid monohydrate in 5 ml. of triethylorthoformate was stirred at 100°-110° C. as 0.7 ml. of DMSO was added. All the solid dissolved. Tlc in (9:1 CHCl₃-MeOH) immediately after dissolution indicated complete reaction. After 5 minutes, at 110°-115° C., the solution was cooled, resulting in crystallization of product. After dilution with ethanol the solid was collected on a filter and washed with ethanol and with ether. Yield of yellow crystals = 130 mg. (51%), m.p. 230°-233° C., (dec.) Tlc (9:1 CHCl₃-MeOH) showed a single spot.

Although this invention has been described in relation to specific embodiments, it will be apparent that obvious modifications may be made by one skilled in the art without departing from the intended scope thereof as defined by the appended Claims.

What is claimed is:

1. A composition useful against coccidiosis that comprises a solid nutritive poultry feed having intimately dispersed therein an effective amount of 5-deazariboflavin or a derivative thereof having the structure:

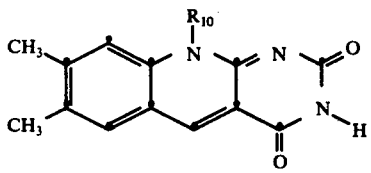

wherein $R_{10}$ is:

wherein $R_5$ is H or

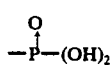

and non-toxic salts thereof; or $R_{10}$ is:

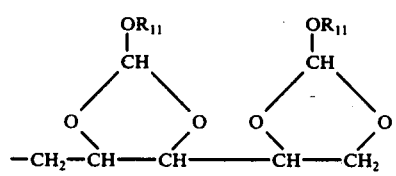

wherein $R_{11}$ is an alkyl group containing 1 to 5 carbon atoms.

2. A composition according to claim 1 wherein $R_{10}$ is:

—CH₂—(CHOH)₃—CH₂OH.

3. A poultry feed premix composition that comprises an inert, solid, nutritive poultry feed having dispersed therein from about 0.1% to about 50% by weight of 5-deazariboflavin or a derivative thereof having the structure:

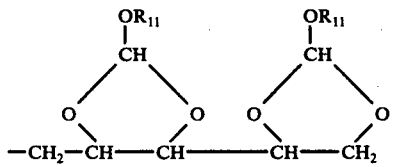

wherein $R_{10}$ is:

wherein $R_5$ is H or

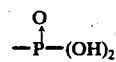

and non-toxic salts thereof; or $R_{10}$ is:

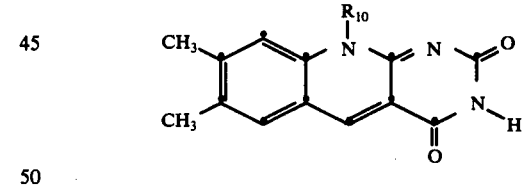

wherein $R_{11}$ is an alkyl group containing 1 to 5 carbon atoms.

4. A composition according to claim 3 wherein said premix composition comprises from about 0.5% to 25% by weight of 5-deazariboflavin or a derivative thereof.

5. A composition according to claim 3 wherein $R_{10}$ is:

—CH₂—(CHOH)₃—CH₂OH.

6. A composition according to claim 4 wherein $R_{10}$ is:

—CH₂—(CHOH)₃—CH₂OH.

7. A composition for treating coccidiosis comprising poultry feedstuff containing an effective amount of 5-deazariboflavin or a derivative thereof having the structure:

wherein $R_{10}$ is:

wherein $R_5$ is H or

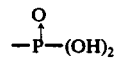

and non-toxic salts thereof; or $R_{10}$ is:

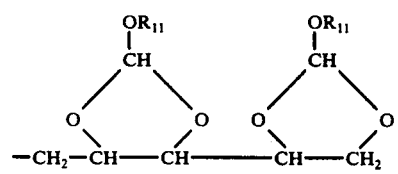

wherein $R_{11}$ is an alkyl group containing 1 to 5 carbon atoms.

8. A poultry feedstuff according to claim 7 wherein $R_{10}$ is:

—CH$_2$—(CHOH)$_3$—CH$_2$OH.

9. A composition for treating coccidiosis comprising an animal feedstuff having dispersed therein about 0.0005% by weight of 5-deazariboflavin or a derivative thereof having the structure:

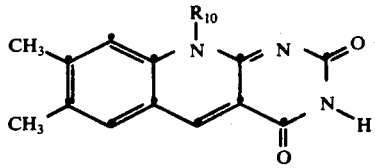

wherein $R_{10}$ is:

—CH$_2$—(CHOH)$_3$—CH$_2$OR$_5$ wherein $R_5$ is H or

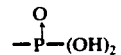

and non-toxic salts thereof; or $R_{10}$ is:

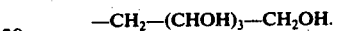

wherein $R_{11}$ is an alkyl group containing 1 to 5 carbon atoms.

10. An animal feedstuff according to claim 9 wherein $R_{10}$ is:

—CH$_2$—(CHOH)$_3$—CH$_2$OH.

11. An animal feedstuff according to claim 9 having dispersed therein about 0.001% to 0.006% by weight of 5-deazariboflavin.

* * * * *

UNITED STATES PATENT AND TRADEMARK OFFICE
CERTIFICATE OF CORRECTION

PATENT NO. : 4,053,602

DATED : October 11, 1977

INVENTOR(S) : Donald W. Graham, Edward F. Rogers and Wallace T. Ashton

It is certified that error appears in the above-identified patent and that said Letters Patent are hereby corrected as shown below:

At Col. 7, line 39 insert --- 3. Results ---

At Col. 11, line 9 after 0.0005% insert ---to 0.05% ---.

Signed and Sealed this

Fourteenth Day of February 1978

[SEAL]

Attest:

RUTH C. MASON
*Attesting Officer*

LUTRELLE F. PARKER
*Acting Commissioner of Patents and Trademarks*